(12) United States Patent
Classen

(10) Patent No.: US 8,795,512 B2
(45) Date of Patent: Aug. 5, 2014

(54) METHOD FOR MEASURING AND/OR CALIBRATING A GAS SENSOR

(75) Inventor: Thomas Classen, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 13/272,953

(22) Filed: Oct. 13, 2011

(65) Prior Publication Data
US 2012/0097553 A1 Apr. 26, 2012

(30) Foreign Application Priority Data
Oct. 20, 2010 (DE) .......................... 10 2010 042 701

(51) Int. Cl.
*G01N 27/419* (2006.01)
(52) U.S. Cl.
USPC ........ 205/781; 205/783; 205/784; 205/784.5; 73/1.06; 73/23.31; 123/676; 123/703
(58) Field of Classification Search
USPC ......... 204/401, 406, 408, 409–412, 415–416, 204/421–430; 205/775.5, 778.5, 205/780.5–781, 782–787; 73/1.01–1.04, 73/4.06, 23.31, 23.32, 1.06; 123/672, 676, 123/703–704
See application file for complete search history.

(56) References Cited

U.S. PATENT DOCUMENTS

| | | | |
|---|---|---|---|
| 3,650,934 A | 3/1972 | Hickam et al. | |
| 2003/0136676 A1* | 7/2003 | Miwa et al. | 204/426 |
| 2008/0296174 A1* | 12/2008 | Ding et al. | 205/781 |
| 2011/0314898 A1* | 12/2011 | Liemersdorf et al. | 73/23.31 |

FOREIGN PATENT DOCUMENTS

| | | |
|---|---|---|
| EP | 0 878 709 | 11/1998 |
| JP | 2008170316 | 7/2008 |
| WO | WO 2010003826 A1 * | 1/2010 |

* cited by examiner

*Primary Examiner* — Susan D Leong
(74) *Attorney, Agent, or Firm* — Kenyon & Kenyon LLP

(57) ABSTRACT

A method for measuring and/or calibrating a gas sensor for determining oxygenic gas components in gas mixtures in exhaust gases of internal combustion engines. The gas sensor has one internal pump electrode IPE, one external pump electrode APE and one decomposition electrode NOE. The measurement and/or calibration may be carried out during the ongoing operation of the gas sensor by removing the gas component and/or oxygen from one of the chambers, by introducing oxygen in a controlled manner into one of the chambers with the aid of electrochemical pumping processes. The changes caused by the introduced oxygen are measured against an additional electrode and the gas sensor may be measured and/or calibrated using the measured values.

20 Claims, 3 Drawing Sheets

METHOD FOR MEASURING AND/OR CALIBRATING A GAS SENSOR

CROSS REFERENCE

The present application claims the benefit under 35 U.S.C. §119 of German Patent Application No. DE 102010042701.2 filed on Oct. 20, 2010, which is expressly incorporated herein by reference in its entirety.

FIELD OF THE INVENTION

The present invention relates to a method for measuring and/or calibrating a gas sensor provided for determining, in particular, oxygenic gas components in gas mixtures.

BACKGROUND INFORMATION

Due to environmental consciousness, which has increasingly grown in the past few years, and thanks to various technical developments, it was possible to significantly reduce the amount of harmful substances in the exhaust gases of internal combustion engines. Nitrogen oxides (NO, $NO_2$, in general $NO_x$), a significant part of which may be reduced to nitrogen during an after-treatment of exhaust gases, for example with the aid of selective catalytic reduction, continue to be an important emission class. In order to be able to analyze and optimize the composition of exhaust gases, in particular with regard to their after-treatment, it is necessary to accurately determine the concentration of the harmful substances, e.g., of the nitrogen oxides, contained in the exhaust gas. Here, even the smallest quantities of harmful substances, e.g., in the ppm range, need to be reliably determinable.

However, detecting nitrogen oxides is not an easy task due to the high amount of oxygen also being present in the exhaust gas. For measuring small nitrogen oxide concentrations in the simultaneous presence of oxygen, $ZrO_2$-based solid electrolyte sensors are usually used. Such a sensor is provided with multiple sections or chambers which are generally separated from each other via diffusion barriers. Here, the oxygen concentration is reduced in a first chamber to a predetermined value by a first electrolytic oxygen pump cell. The pump voltage is applied to the electrolyte in such a way that the resulting electric potential in the electrolyte drives a flow of oxygen ions out of the chamber. By selecting the physical conditions, such as the temperature, the catalytic effect of the electrode material and the variable of the applied pump voltage, it is achieved that the nitrogen oxides, as oxygenic compounds or other oxygenic compounds to be determined, are not decomposed or only a small amount of them is decomposed, and they do not contribute or only contribute to a reduced extent to the oxygen pumping flow out of the first chamber. In another chamber, another electrolytic pump cell further reduces the oxygen concentration to such an extent that the nitrogen oxides, being oxygenic compounds, are dissociated into oxygen and nitrogen. The electric current arising by the pumping of oxygen, usually ranging between nA and µA, is measured and represents a measure for the nitrogen oxide concentration in the measured gas. For pumping out the oxygen alone, one or multiple internal pump electrodes (IPE) may be provided which are situated in one or multiple first chamber(s). The other electrode, through which the decomposition of the nitrogen oxides takes place, is also referred to as a decomposition electrode (NOE).

In nitrogen oxide concentrations of only a few ppm, the amount of the electric current to be measured is usually very small, e.g., only few nA, so that even the smallest interferences have a dramatic effect. In particular, leakage currents at the sensor itself, at the sensor housing or in the cable may be erroneously interpreted as an $NO_x$ current. In order to compensate for that, a complex calibration is usually performed after manufacturing $NO_x$ sensors of this type. The calibration result is stored in a memory assigned to the sensor, usually in the sensor evaluation electronics. Over the lifetime of the sensor, however, shifts may develop, which falsify the basis value of the $NO_x$ signal and its gradient, due to various aging phenomena such as change in the internal resistance, electrode aging, temperature drift, change in the contacts/insulation resistances, etc. Furthermore, an increased burst of oxygen to the decomposition electrode may result in a change in the $NO_x$ signal. If this burst has not already occurred during the starting calibration, the burst will cause significant measuring errors during ongoing operation.

In order to prevent problems of this type, it is desirable to be able to perform in-situ recalibration of an $NO_x$ sensor during operation. This is, however, difficult because there is no independent measurement of the $NO_x$ value which might be used for calibration. The conventional nitrogen oxide sensors additionally have a cross sensitivity to $NH_3$. During the normal driving cycle, a state never occurs in which neither $NO_x$ nor $NH_3$ reliably prevails, so that the measuring signal might be unambiguously assigned to either $NO_x$ or $NH_3$.

Against this backdrop, an object of the present invention is to provide a method for calibrating an $NO_x$ sensor or other sensors for determining, in particular, oxygenic gas components, which allows the sensor to be measured or calibrated during ongoing operation, so that sensor changes occurring over the operating time of the sensor may be taken into account. This object may be achieved with the aid of an example method for measuring and/or calibrating a gas sensor which is provided for determining, in particular, oxygenic gas components in gas mixtures according to the present invention.

SUMMARY

An example method according to the present invention is based on the fact that the sensor is set to a changed operating mode for a short period of time, external changes, related to the composition of the exhaust gas or the measured gas, being "suppressed." For this purpose, oxygen and, if necessary, other gas components of the measured gas are initially removed from the sensor with the aid of electrochemical pumping processes. Subsequently, the oxygen is transported in a controlled manner into one or multiple chambers of the sensor, and the thus resulting changes are measured. The results may be indicative of certain sensor properties, and the gas sensor may be calibrated accordingly, if necessary. The method according to the present invention is therefore used for in-situ measurement and/or calibration of a gas sensor which is provided for determining, in particular, oxygenic gas components such as nitrogen oxides, in gas mixtures, in particular in exhaust gases of internal combustion engines.

The gas sensor has at least one internal electrode (IPE) in the form of an internal pump electrode, at least one external electrode (APE) in the form of an external pump electrode, and at least one decomposition electrode (NOE) provided for electrochemically decomposing the gas component to be determined. The at least one internal electrode (IPE) and the at least one decomposition electrode (NOE) are provided in chambers or sections of the gas sensor separate from one another. An ion flow induced at the decomposition electrode by the decomposition of the gas component to be determined, in particular an oxygen flow, is used to determine the concentration of the gas component. According to an example embodiment of the present invention, the gas sensor is measured and/or calibrated during the ongoing operation by generally removing the gas component to be determined and/or oxygen from at least one of the chambers or sections with the aid of electrochemical pumping processes in a step (a). In a step (b), electrochemical pumping processes are used to introduce oxygen in a controlled manner into at least one of the chambers or sections. The changes caused by the introduced oxygen are measured against an additional electrode, e.g., a reference electrode or another electrode, and the gas sensor or its properties are measured and/or calibrated using the measured values. This example method according to the present invention changes the protective circuit of the electrodes for a short period of time in such a way that it allows calibration measurement of the sensor properties instead of $NO_x$ measurement, so that the sensor parameters may be recalibrated. The calibration may thus take place during the ongoing operation of the gas sensor. Changes in the sensor properties occurring over the lifetime of a gas sensor due to various aging phenomena may be detected and compensated for, so that the gas sensor keeps its measuring accuracy. In this context, calibration is understood to mean measuring and detecting the technical properties of the sensor which are relevant for the measurement. These data are evaluated, stored, and taken into account for ensuring a proper operation.

Preferably, removal of the oxygen and, if necessary, of the gas component to be determined by applying a pump voltage between one of the internal pump electrodes or the decomposition electrode and the external pump electrode, or the additional electrode, a reference electrode (RE), in particular, is carried out in step (a), pump voltages or pump currents being preferably applied. Suitable voltages range, for example, between 1 mV and 3000 mV, in particular between 200 mV and 1200 mV. A voltage between 400 mV and 900 mV is particularly preferred. The electrical field resulting in the electrolyte causes oxygen ions to flow out of the chamber. Alternatively, a current-guided pumping process may be carried out with the aid of the electrodes. Suitable currents range, for example, between 0.1 nA and 100 mA, in particular between 1 nA and 1 mA, and are particularly preferred between 1 nA and 10 µA. With decreasing oxygen concentration, the nitrogen oxides or other oxygenic gas components continue to be decomposed into oxygen and nitrogen or, if applicable, into other molecules, resulting in all of the unbound and bound oxygen molecules being removed from the chamber, in this step.

In order to introduce oxygen in a controlled manner into at least one of the chambers or sections of the gas sensor in step (b), in one specific embodiment, a pump voltage and/or a pump current is/are applied between the additional electrode, e.g., the reference electrode or another electrode, and one of the internal pump electrodes IPE. In another specific embodiment, the pump voltage and/or the pump current is/are applied between the additional electrode and the decomposition electrode or, if applicable, between the additional electrode and an electrode in an accumulation chamber, in order to introduce oxygen.

The electrochemical pumping processes are particularly advantageous if they are periodical and/or pulsed. This mainly applies to introducing oxygen in step (b). By pumping the oxygen periodically, misinterpretations due to circulating flows are prevented at the sensor.

The changes caused by the introduced oxygen may, for example, be measured, in particular, potentiometrically or amperometrically at at least one of the internal pump electrodes IPE and/or at the decomposition electrode NOE and/or at one of the chamber electrodes of the accumulation chamber. The detectable changes in the current and/or in the voltage may thus be used, in particular, for measuring the different diffusion barriers between the individual chambers or sections of the sensor.

It is particularly advantageous to consecutively induce the electrochemical pumping processes at different electrodes of the sensor, in order to be able to measure the individual diffusion barriers separately from one another, for example.

In one example embodiment of the method according to the present invention, oxygen is pumped electrochemically in a predefinable amount and/or at a predefinable rate and/or over a predefinable time interval. Thus, it is possible to monitor the electrode properties by repeatedly introducing oxygen in differing amounts. If a diffusion barrier between two electrodes is highly permeable, it may be easily examined how efficient pumping of the oxygen with the aid of the electrodes may be. An electrode which is close to losing its pumpability pumps the oxygen provided by another electrode only incompletely or at a slower rate.

The gas sensor, which is measured and/or calibrated according to the present invention, is preferably a conventional nitrogen oxide sensor, in particular a double-chamber sensor or a sensor having an accumulation cell. Sensors of this type are often used in the exhaust gas system of motor vehicles, and may be used particularly advantageously for the example method according to the present invention.

Furthermore, the present invention includes an example computer program which executes all the steps of the described example method according to the present invention, if it runs on a computer or a control unit of an internal combustion engine. Finally, the present invention includes an example computer program product having program code stored in a machine-readable carrier for carrying out the example method according to the present invention. This computer program or the computer program product may be used particularly advantageously for measuring and/or calibrating a gas sensor, in order to be able to analyze and, if necessary, calibrate the gas sensor during the ongoing operation. Therefore, the measuring accuracy of the sensor may be significantly improved even during the ongoing operation, so that the sensor keeps its full functionality and measuring accuracy over its entire lifetime. The particular advantage of the computer program is the fact that the computer program may be readily uploaded and used even in existing vehicles, without the need for installing additional system components.

Further advantages and features of the present invention are derived from the following description of exemplary embodiments with reference to the figures. Here, the different features may be implemented individually or in combination with each other.

DETAILED DESCRIPTION OF EXAMPLE EMBODIMENTS

Figure 1:
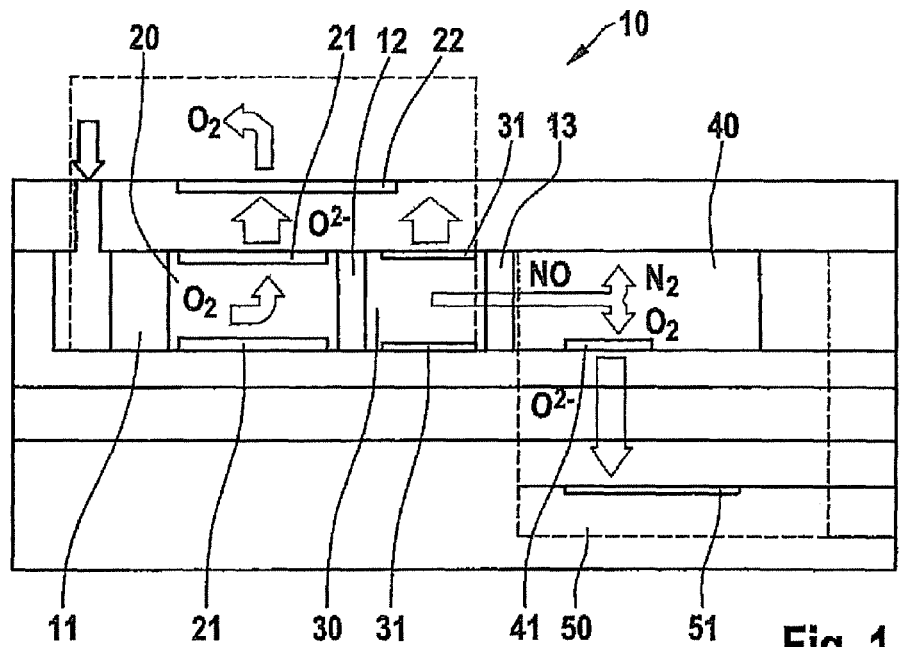
FIG. 1 schematically shows a conventional double chamber nitrogen oxide sensor.

The operation of a conventional double chamber nitrogen oxide sensor is illustrated in the following based on FIG. 1.

Nitrogen oxide sensor 10 includes a first chamber 20 having a first internal pump electrode pair (IPE1) 21. In a second chamber 30, another internal pump electrode pair (IPE2) 31 is provided. In a third chamber 40, an $NO_x$ electrode 41 is situated as a decomposition electrode provided for decomposing the nitrogen oxides. An external pump electrode (APE) 22 is situated facing the exhaust gas. A reference electrode (RE) 51 is provided in an air reference channel 50 or a pumped reference cell. During a normal conventional operation, the exhaust gas mixture enters chamber 20 of the sensor in this diagram from above on the left side of sensor 10 through a first diffusion barrier 11. A voltage between first internal pump electrode 21 and external pump electrode 22 or also reference electrode 51 is used to remove the oxygen from the exhaust gas mixture. Furthermore, second internal pump electrode 31 may be used for further oxygen reduction in the residual gas entering through diffusion barrier 12. Parallel, the oxygen content may be potentiometrically determined via first internal pump electrode 21 and/or via second internal pump electrode 31 against a known reference, against reference electrode 51, for example. Subsequently, downstream from second internal pump electrode 31 and downstream from third diffusion barrier 13, a gas without an oxygen content or at least having a known, very small oxygen content prevails. At decomposition electrode 41, the nitrogen oxides of the gas mixture are decomposed into nitrogen and oxygen. The resulting oxygen is pumped through the solid electrolyte of sensor 10 to reference electrode 51, for example, in the form of an ion flow. The resulting current is indicative of the nitrogen oxide concentration.

Diffusion barriers 11, 12 and 13 may be designed as porously filled spaces or, for example, also as chamber paths or channels or as areas narrowing in the cross section. Depending on the embodiment of the sensor, diffusion barriers 12 and 13 may virtually be omitted.

According to an example embodiment of the present invention, the protective circuit of such a sensor or another sensor provided for determining particularly oxygenic gas components in gas mixtures is changed in such a way that instead of measuring oxygenic gas components, $NO_x$ for example, a measurement is carried out to measure and/or calibrate the sensor.

Figure 2:
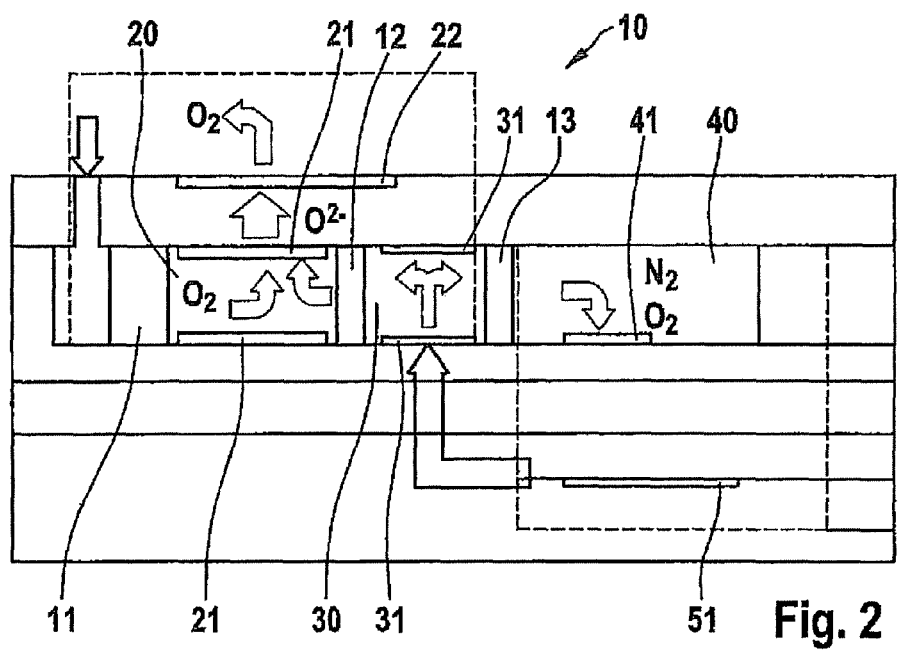
FIG. 2 schematically shows the double chamber nitrogen oxide sensor from FIG. 1, and the ion flows according to an example embodiment of the present invention.

FIG. 2 shows an exemplary implementation of the example method according to the present invention and illustrates the pumping processes resulting in the sensor shown in FIG. 1. After the measured gas has entered first chamber 20 of sensor 10 through diffusion barrier 11, all reducible measured gas components are approximately completely reduced by applying a pump voltage and/or a pump current between electrodes 21 and 22, i.e., first internal pump electrode 21 and external pump electrode 22, and, if necessary, additional internal pump electrodes, and the resulting ion flow is discharged from chamber 20 in the direction of the exhaust gas. In this step (a) the reducible gas components are removed either completely or almost completely, or the concentration of the reducible components is reduced to a sufficiently small amount. The voltage at electrodes 21, 22 and/or 31, 22 and/or 41 is increased to such an extent that oxygen and other oxygenic gas components, in particular $NO_x$, are virtually completely decomposed. Depending on the embodiment of the method according to the present invention, small or very small concentrations of these gas components may remain for practical reasons. By removing the oxygenic gas components including the molecular oxygen, the processes in the sensor are decoupled from the external conditions in a first approximation. Preferably, this step should be carried out under known and preferably unchanged external conditions, in order to prevent even small, e.g., electrical, interferences. Since the internal electrodes, in particular internal pump electrodes 21 and 31 as well as decomposition electrode 41 are decoupled after the step (a) from the actual composition of the measured gas, i.e., the exhaust gas, the electrodes may be used for calibration measurements. Here, oxygen is initially pumped in a controlled manner into at least one of chambers 20, 30 and/or 40 in a step (b). The oxygen may be removed as molecular oxygen ($O_2$) or used for saturating fatty gas components ($H_xC_y$, CO, $H_2$, . . . ), CO to $CO_2$, for example. The type of reaction depends on the instantaneous gas composition in the surroundings of the removing electrode. Under the typical operating conditions of an $NO_x$ sensor, the molecular oxygen is typically removed; however, fatty gas conditions may be set beforehand in a controlled manner for calibration purposes, if necessary. In order to introduce the oxygen into the chambers of sensor 10, the oxygen is, for example, transported between reference electrode 51 and second internal pump electrode 31 by applying a pump voltage and/or a pump current, as indicated in FIG. 2.

Other internal pump electrode 21 or decomposition electrode 41 may also be used for this purpose, for example. Some of the removed oxygen reaches first internal pump electrode 21 in chamber 20 through diffusion barrier 12. There, the oxygen may be detected through the resulting increase in current, if the external influences are sufficiently constant and the amount of oxygen accumulated at second internal pump electrode 31 is adequate. The oxygen is preferably removed periodically or in clocked mode, or by pulsed pumping, allowing an evaluation similar to a lock-in principle at first internal electrode 21, so that influences which do not have the right frequency may be filtered out. Other types of pulsing or current paths are also possible. The amount of the arriving oxygen is measured in relation to the introduced amount. The time curve and the phase shift of the detection signal in the case of periodic operation in relation to the introduction may, as a propagation time measurement, provide additional information about the properties of the diffusion barriers. If the geometry of the excitation is known, the value of these parameters may be ascertained from a simplified diffusion model containing one or multiple free parameters, for example, which represent diffusion coefficients or the temperature, for example, and from the actually measured increase in oxygen at electrode 21. In this way, the diffusion properties of second diffusion barrier 12 may be examined and calibrated.

Another part of the removed oxygen reaches decomposition electrode 41 through a third diffusion barrier 13 after leaving chamber 30. This oxygen flow may be pumped out and analyzed via the decomposition electrode, so that the diffusion properties of third diffusion barrier 13 may be measured. The oxygen is pumped out preferably periodically at decomposition electrode 41 for measuring the flow, in order to prevent circulating flows in sensor 10. For measuring the properties of third diffusion barrier 13, the protective circuit may be designed, for example, in such a way that the oxygen is pumped from first internal pump electrode 21 to second internal pump electrode 31, and from decomposition electrode 41 to reference electrode 51, preventing circulating flows once again.

The formation of the oxygen at second internal pump electrode 31 is preferably implemented via a current source (not shown). If necessary, it may be checked which oxygen concentration instantaneously prevails at second internal pump electrode 31 by potentiometrically measuring the voltage against a known reference, reference electrode 51 or external pump electrode 22, for example.

Additionally or alternatively, decomposition electrode 41 may also similarly be used as the removing electrode. For this purpose, a pump current may be applied between decomposition electrode 41 and reference electrode 51, for example. The changes in the current of pumping-out second internal pump electrode 31 and first internal pump electrode 21, in the direction of external pump electrode 22, for example, may be similarly used for measuring third diffusion barrier 13 and second diffusion barrier 12.

Measuring first diffusion barrier 11 is also possible if, for example, the oxygen concentration of the exhaust gas is known through a lambda sensor installed in the exhaust gas system. In this case, the diffusion constant of first diffusion barrier 11 may be determined via the pump current at first internal pump electrode 21. Alternatively, through the formation of a proportionally large amount of oxygen at first internal pump electrode 21 and measurement at second internal pump electrode 31, it may be determined how much oxygen flows proportionately from first internal pump electrode 21 through first diffusion barrier 11. Here, the external influences should, however, remain generally constant over time. If the properties of second diffusion barrier 12 and, if necessary, of third diffusion barrier 13 are known or previously calibrated, the diffusion properties of first diffusion barrier 11 may be inferred herefrom in relation to second diffusion barrier 12. Thus, if first diffusion barrier 11 is relatively tight, the main portion of the oxygen will flow off through second diffusion barrier 12, so that it may be accurately ascertained from the absolute current at second internal pump electrode 31 as compared to the metered oxygen how much oxygen is diffused through first diffusion barrier 11.

The conversions of the limiting current signals to $O_2$ and $NO_x$ concentrations may be calibrated using the measurable properties, according to an example embodiment of the present invention, of the different diffusion barriers. Here, the current measuring signals (nA) are calibrated to the concentration of $NO_x$ (ppm). Furthermore, the zero value of decomposition electrode 41 may be determined in the state when all oxygen and all nitrogen oxides are decomposed at first internal pump electrode 21, so that the cross and leakage currents not caused by $NO_x$ become detectable. From this value and the measurement of the diffusion barriers, the $NO_x$ signal may be calibrated by recirculation.

In addition, the method according to the present invention allows the detection of additional information. A reduced diffusivity over time indicates that the diffusion barriers are clogged. An increased diffusivity over time is indicative of excess temperature of the sensor. If the diffusion barriers do not all change in the same way, conclusions may be drawn, e.g., about the change in the sensor temperature, such as through aging of the heater, or changes in the temperature measurement, or about contamination.

By repeatedly metering the oxygen in changing amounts, the properties of the different electrodes may be monitored. In particular, if a diffusion barrier located between two electrodes is highly permeable, the efficiency of the electrodes during the pumping out of the oxygen may be accurately detected. Thus, an electrode which is close to losing its pumpability pumps the oxygen provided by another electrode only incompletely or at a slower rate. For example, oxygen may form in a linearly increasing amount per pulse at second internal pump electrode 31 in a series of preferably pulsed pumping processes. The pumping-out signal of decomposition electrode 41 is simultaneously observed. An accordingly linearly increasing curve will be observed in the case of a non-aged electrode. In the case of an aged electrode, a sublinear behavior may result starting from a certain amount, for example. The maximum, still linear pumpage is indicative of the pumpability of decomposition electrode 41. Similarly, this procedure is also usable conversely or with other adjacent electrodes.

Figure 3:
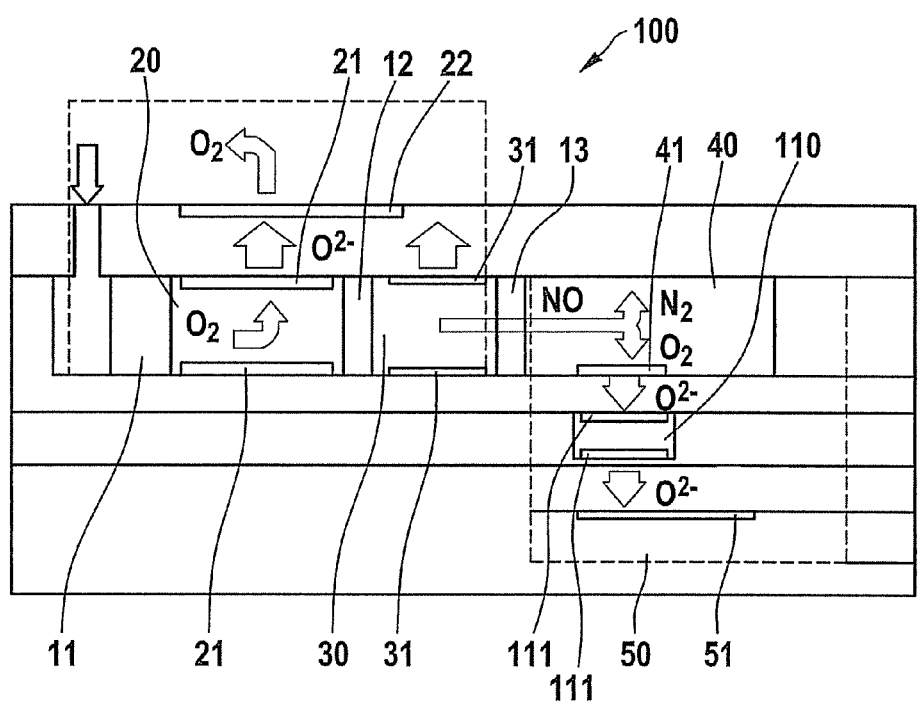
FIG. 3 schematically shows a nitrogen oxide sensor having an accumulation chamber for further illustrating the example method according to the present invention.

The method according to the present invention is also advantageously usable with a gas sensor, e.g., a conventional nitrogen oxide sensor, having an accumulation chamber. A nitrogen oxide sensor 100 having an accumulation cell or accumulation chamber 110, as schematically shown in FIG. 3, has a comparable system of chambers, electrodes, and diffusion barriers as double chamber sensor 10 illustrated in FIGS. 1 and 2. The corresponding elements of sensor 100 having accumulation cell 110 are designated with the same reference numerals as in FIGS. 1 and 2. Moreover, sensor 100 has accumulation chamber 110 in which one or multiple chamber electrode(s) 111 is/are located. For the nitrogen oxide measurement, after removing the oxygen at internal pump electrodes 21 and 31, the nitrogen oxides are decomposed into nitrogen and oxygen in chamber 40 by applying or generating a proportionally high voltage at decomposition electrode 41. The oxygen is pumped by decomposition electrode 41 to chamber electrode 111 in the form of an ion flow and is thus transported into accumulation chamber 110. In accumulation chamber 110, the oxygen is concentrated (accumulated) and may be measured as a measure for the nitrogen oxide concentration in the measured gas. The oxygen concentration may, for example, be measured with the aid of an amperometrical measurement (pumping out) between chamber electrode 111 and reference electrode 51, or with the aid of a potentiometrical measurement (voltage measurement against a reference, e.g., reference electrode 51) of the content of accumulation chamber 110. Due to the accumulation of the very small amounts of oxygen in accumulation chamber 110, seen from an absolute viewpoint, even very small nitrogen oxide concentrations may be detected. Such a nitrogen oxide sensor 100, which is known per se, is also usable for in-situ measurement and/or calibration according to the method according to the present invention. Here, chamber electrodes 111 in accumulation chamber 110 are usable as sources when pumping to second internal pump electrode 31, to decomposition electrode 41 or to first internal pump electrode 21, and also as target electrodes when pumping out from decomposition electrode 41, from second internal pump electrode 31, from first internal pump electrode 21 or from additional electrodes such as reference electrode 51 or external pump electrode (APE) 22. After formation of the oxygen in step (b) of the method according to the present invention, at second internal pump electrode 31, for example, the accumulation of oxygen may also be measured in accumulation chamber 110 with the aid of a pump voltage between decomposition electrode 41 and chamber electrode 111, instead of measuring the current between decomposition electrode 41 and reference electrode 51. Based on a known amount of oxygen which has formed in step (b), the properties of accumulation chamber 110 may also be measured and calibrated.

Alternatively or additionally, a known amount of oxygen may have formed as a known load quantity at chamber electrode(s) 111. By subsequently measuring the content of chamber 110 potentiometrically or amperometrically, the chamber volume of accumulation chamber 110 may be calibrated. Finally, if the chamber volume is known, accumulation chamber 110 itself may also be used for generating an exactly defined amount of oxygen. For this purpose, the content of accumulation chamber 110 is reduced by a certain amount of oxygen. This takes place, in particular, by pumping out to one of the electrodes of the sensor, e.g., to second internal pump electrode 31, at which an equivalent amount of oxygen, which is exactly known with the aid of the chamber volume, is formed. This replaces a precise current source in the control electronics of sensor 100, so that this embodiment of the method according to the present invention is particularly advantageous for reasons of cost.

Figure 4:
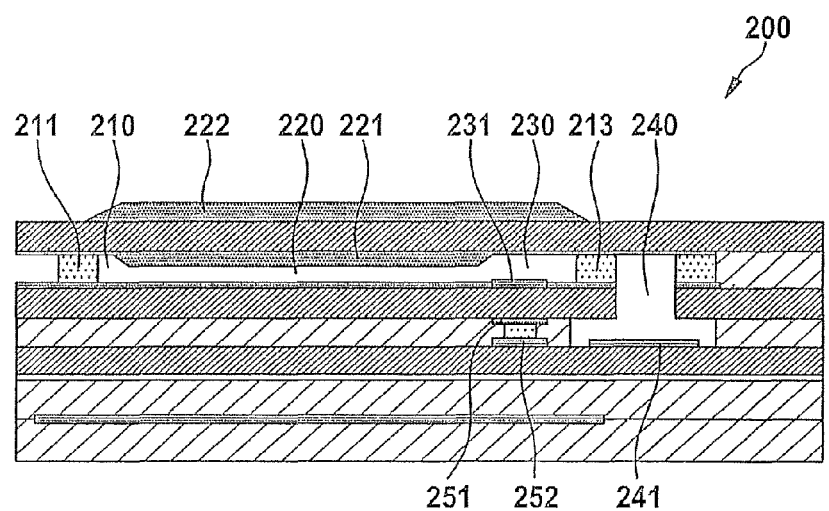
FIG. 4 schematically shows an additional nitrogen oxide sensor.

Another design of a conventional nitrogen oxide sensor is shown in FIG. 4. This design of a conventional nitrogen oxide sensor 200 described in Japanese Patent Application No. JP 2008 170316 A, for example, shows an arrangement of areas 210 and 240 in two layers of sensor 200. This arrangement of areas 210 and 240 allows insulating layers to be provided for electrically isolating the cells of sensor 200. This allows the lines to be combined and to thus save connection terminals. The method according to the present invention may, for example, also be used in such a nitrogen oxide sensor in order to be able to conduct an in-situ calibration. In particular, area 210 contains multiple electrodes having different functions behind diffusion barrier 211 and may be regarded as a system which includes an anterior chamber area 220 and a posterior chamber area 230, a diffusion path possibly lying between the two chamber parts or the two parts merging smoothly into one another. Area 240 is situated in another layer plane of the sensor, but is linked to chamber area 230 via a diffusion barrier 213. In order to remove oxygen streaming in from the outside in a controlled manner, electrode 221 in chamber part 220 may be used together with counter electrode 222 on the top, for example. In order to introduce oxygen in a controlled manner into chamber part 230, for example, electrode 231 may be used. This electrode 231 is generally used as a measuring electrode during conventional operation of nitrogen oxide sensor 200. According to the present invention, electrode 231 may, however, also assume a pumping function for introducing oxygen into chamber part 230. One of electrodes 251 or 252, for example, may be used as a reference electrode. Alternatively, the oxygen may be introduced at electrode 241 in area 240 and a measurement may take place at electrode 231 or other combinations may be used.

The method according to the present invention is not limited to nitrogen oxide sensors. It may also be used for measuring and calibrating other gas sensors which are used for determining other gas components. For example, the method according to the present invention may be used for calibrating a multi-chamber HC sensor. Here, the assembly is similar in principle; the electrodes are, however, typically manufactured from different materials, and other pump voltages are used during normal operation. Here, too, diffusion barriers may be calibrated with the aid of oxygen formation or fatty gas saturation at an electrode, as well as the detection of the change in the gas composition at another electrode.

What is claimed is:

1. A method for measuring and/or calibrating a gas sensor which is provided for determining an oxygenic gas component in exhaust gases of an internal combustion engine, the gas sensor having at least one internal electrode, at least one external electrode, and at least one decomposition electrode for electrochemically decomposing the gas component to be determined, the at least one internal electrode and the at least one decomposition electrode being situated in chambers or sections of the gas sensor which are separate from one another, and an ion flow, which is induced by the decomposition of the gas component to be determined, being used for determining the gas component, the method being carried out during ongoing operation of the gas sensor and comprising:

removing at least one of the gas component to be determined and oxygen from at least one of the chambers or sections with the aid of an electrochemical pumping process;

introducing oxygen in a controlled manner into at least one of the chambers or sections with the aid of electrochemical pumping processes;

measuring changes caused by the introduced oxygen against an additional electrode; and at least one of measuring and calibrating the gas sensor using values obtained via the measuring;

wherein the changes are measured at a chamber electrode; and wherein the chamber electrode is positioned in a separate chamber from the at least one internal electrode, the at least one external electrode, and the at least one decomposition electrode.

2. The method as recited in claim 1, wherein the removal of the at least one of the gas component to be determined and the oxygen is carried out by applying at least one of a pump voltage and a pump current between one of: i) one of the at least one internal electrodes and the external pump electrode, or ii) one of the at least one internal electrode and the additional electrode.

3. The method as recited in claim 1, wherein the removal of the at least one of the gas component to be determined and the oxygen is carried out by applying a voltage of between 1 mV and 3V between one of: i) one of the at least one internal electrodes and the external pump electrode, or ii) one of the at least one internal electrodes and the additional electrode.

4. The method as recited in claim 1, wherein the removal of the at least one of the gas component to be determined and the oxygen is carried out by applying a voltage of between 200 mV and 1.2V between one of: i) one of the at least one internal electrodes and the external pump electrode, or ii) one of the at least one internal electrodes and the additional electrode.

5. The method as recited in claim 1, wherein the removal of the at least one of the gas component to be determined and the oxygen is carried out by applying a voltage of between 400 mV and 900 mV between one of: i) one of the at least one internal electrodes and the external pump electrode, or ii) one of the at least one internal electrodes and the additional electrode.

6. The method as recited in claim 1, wherein the removal of the at least one of the gas component to be determined and the oxygen is carried out by applying a current of between 0.1 nA and 100 mA between one of: i) one of the at least one internal electrodes and the external pump electrode, or ii) one of the at least one internal electrodes and the additional electrode.

7. The method as recited in claim 1, wherein the removal of the at least one of the gas component to be determined and the oxygen is carried out by applying a current of between 1 nA and 1 mA between one of: i) one of the at least one internal electrodes and the external pump electrode, or ii) one of the at least one internal electrodes and the additional electrode.

8. The method as recited in claim 1, wherein in the introducing step, at least one of a pump voltage and a pump current is applied between the additional electrode and one of the at least one internal pump electrode for introducing oxygen in a controlled manner into at least one of the chambers or sections.

9. The method as recited in claim 1, wherein in the introducing step, at least one of a pump voltage and a pump current is applied between the additional electrode and the decomposition electrode for introducing oxygen in a controlled manner into at least one of the chambers or sections.

10. The method as recited in claim 1, wherein in the introducing step, at least one of a pump voltage and a pump current is applied between the additional electrode and a chamber electrode for introducing oxygen in a controlled manner into at least one of the chambers or sections.

11. The method as recited in claim 1, wherein the electrochemical pumping processes occur at least one of periodically, clocked, and pulsed.

12. The method as recited in claim 1, wherein the changes are measured at the at least one of the internal pump electrodes.

13. The method as recited in claim 1, wherein the changes are measured at the decomposition electrode.

14. The method as recited in claim 1, wherein the measurements measure properties of diffusion barriers between the chambers or sections of the gas sensor.

15. The method as recited in claim 1, wherein the electrochemical pumping processes are induced consecutively at different electrodes.

16. The method as recited in claim 1, wherein oxygen is pumped electrochemically in at least one of a predefinable amount, at a predefinable rate, and over a predefinable time interval.

17. The method as recited in claim 1, wherein different oxygen amounts are electrochemically pumped in multiple measuring passes.

18. The method as recited in claim 1, wherein the gas sensor is a nitrogen oxide sensor.

19. The method as recited in claim 18, wherein the nitrogen oxide sensor is a double chamber sensor.

20. The method as recited in claim 18, wherein the nitrogen oxide sensor is a sensor having an accumulation cell.

* * * * *